United States Patent [19]

Reynaud et al.

[11] Patent Number: 5,328,372

[45] Date of Patent: Jul. 12, 1994

[54] PHYSIOLOGICAL DENTAL SECURING PEG OF COMPOSITE MATERIAL AND METHOD OF MANUFACTURE THEREOF

[76] Inventors: Marc Reynaud, 23, avenue de la Plaine Fleurie, 38240 Meylan; Pierre-Luc Reynaud, 77 Rue St Expuery 38600, St. Martin d'Heres; Francois Duret, Draye-des-Vignes, 38690-Le Grand Lemps; Bernard Duret, La Jarnetiere -St-Gervais, 638470-Vinay, all of France

[21] Appl. No.: 856,209

[22] PCT Filed: Nov. 20, 1990

[86] PCT No.: PCT/FR90/00831

§ 371 Date: May 13, 1992

§ 102(e) Date: May 13, 1992

[87] PCT Pub. No.: WO91/07142

PCT Pub. Date: May 30, 1991

[30] Foreign Application Priority Data

Nov. 20, 1989 [FR] France .................. 89 15194

[51] Int. Cl.⁵ .................................. A61C 5/08
[52] U.S. Cl. ...................... 433/220; 433/221
[58] Field of Search .............. 433/220, 221, 225

[56] References Cited

U.S. PATENT DOCUMENTS

| | | | |
|---|---|---|---|
| 4,645,457 | 2/1987 | Goldman et al. | 433/220 |
| 4,684,555 | 8/1987 | Neumeyer | 433/220 X |
| 4,738,616 | 4/1988 | Reynaud | 433/220 |
| 4,952,150 | 8/1990 | Schiwiora et al. | 433/220 |
| 4,990,090 | 2/1991 | Roane | 433/220 |
| 5,073,112 | 12/1991 | Weil | 433/220 X |
| 5,074,792 | 12/1991 | Bernadat | 433/220 |

FOREIGN PATENT DOCUMENTS

| | | | |
|---|---|---|---|
| 0076086 | 4/1983 | European Pat. Off. | 433/225 |
| 3825601 | 3/1989 | Fed. Rep. of Germany | 433/220 |
| 2173350 | 10/1973 | France . | |
| 2587197 | 3/1987 | France | 433/220 |
| 2588181 | 4/1987 | France . | |
| 2626167 | 1/1989 | France . | |
| 1302022 | 1/1973 | United Kingdom | 433/220 |

Primary Examiner—Gene Mancene
Assistant Examiner—Nicholas A. Lucchesi
Attorney, Agent, or Firm—McAulay Fisher Nissen Goldberg & Kiel

[57] ABSTRACT

A crown-root reconstitution system and method of manufacturing a physiological dental securing peg in which a crown reconstituting material (3) is placed between a peg (1) and sound dentine walls (2a). The peg is formed of a composite material and includes high strength fibers (5) embedded parallel to one another, elongated in its axial direction, continuous from one end to the other end thereof. An epoxy resin matrix is formed, and a transverse modulus of elasticity of the order of magnitude of the average of that of the dentine in the amount of 18 GPa and a longitudinal compression-tensile strength and shear strength greater than corresponding average values for the dentine is provided by tensioning all of the fibers equally and pre-stressing all of the fibers in traction. The peg is manufactured by extruding the resin around a wick of continuous fibers which are all equally tensioned and pre-stressed in traction, allowing the resin to harden, cutting the ring of composite material after the resin is hardened, and machining the peg by slicing so as to obtain two coaxial cylindro-conical parts of different diameters, in line with each other, each comprising a cylindrical shank (6, 8) followed by a respective truncated part of a frustrum of a cone (7, 9) converging towards the apex of the peg.

16 Claims, 1 Drawing Sheet

PHYSIOLOGICAL DENTAL SECURING PEG OF COMPOSITE MATERIAL AND METHOD OF MANUFACTURE THEREOF

The present invention relates to a crown-root reconstitution system comprising a physiological dental securing peg made of a composite material and a crown reconstituting material placed between the peg and the sound dentine walls, as well as to a process for manufacturing this peg.

Dental securing pegs which are currently used at the present time in odontology, are generally made of metal alloys. However, these pegs have not proved to be totally satisfactory as, even if they are made of precious alloy, which is often the case for reasons of regulations, they may give rise to phenomena of corrosion and oxidation of a chemical or electrochemical origin.

In order to overcome this drawback, it has already been envisaged, as described in Patent FR-A-2 588 181, to make an endobuccal prosthesis of composite material constituted by fibers of high mechanical strength, included in a resin constituting the matrix of the material. A peg is also known, as described in Patent FR-A-2 626 167, comprising a central thread or filament around which is moulded a synthetic resin which preferably contains fibers. Patent DE-A-3 825 601 likewise discloses a dental securing peg constituted by a piece of revolution made of composite material formed by two parts of different diameters, coaxial in line with each other, the part of smaller diameter being adapted to engage in the root canal of the tooth. The pegs manufactured in this way may be given interesting physical and mechanical characteristics but the pegs thus obtained are not totally satisfactory as their mechanical properties are far away from the natural characteristics of the dentine. The disparity of the mechanical properties between those of the peg and those of the dentine is a constant source of disturbance, with a concentration of the stresses at certain points, and this may result in the destruction of the reconstruction assembly if the stresses applied to this assembly, during chewing, end up by disconnecting the constituent elements.

The present invention aims at overcoming this drawback by providing a reconstitution system which dampens the stresses and distributes them at a maximum in the zones subjected to the efforts.

To that end, this crown-root reconstitution system comprises a physiological dental securing peg of a composite material, and a crown reconstituting material placed between the peg and the sound dentine walls, the peg being constituted by a piece of revolution of the type made of high strength fibers embedded in a resin constituting the matrix, the fibers being parallel to one another, elongated in the axial direction of the peg, continuous from one end of the peg to the other, in the central part of this peg, is characterized in that the resistant fibers are equally tensioned and pre-stressed in traction so that the peg thus obtained presents a transverse modulus of elasticity of the order of magnitude of the average of that of the dentine, namely 18 GPa, and a longitudinal compression-tensile strength and shear strength greater than the corresponding average values for the dentine.

A securing peg according to the invention presents anisotropic mechanical characteristics, i.e. which depend considerably on the direction of application of an effort with respect to the longitudinal direction of the fibers, i.e. of the peg. Thus, such a peg made from high performance carbon fibers embedded in an epoxy resin matrix, has a transverse modulus of elasticity which has a value of 8.5 GPa for an angle of application of the traction effort, with respect to the transverse direction, of 0° and a value of 34 GPa for an angle of 20° which gives an average of 21 GPa in the angular range of 0° to 20° which corresponds to the average orientation of the stresses exerted on a tooth during chewing. This value is close to the transverse modulus of elasticity of the dentine which is 18 GPa. Concerning the compression resistance, it may go up to 500 MPa, i.e. 200 MPa more than the mean resistance of the dentine. Such characteristics are obtained with composite materials of which 100% of the fibers are continuous from one end of the peg to the other and equally tensioned, these fibers representing from 40 to 80% of the total volume of the peg, i.e. of the volume of the fibers themselves and of the resin constituting the matrix. The fibers are preferably high performance carbon fibers and the resins are preferably epoxy or polyester resins. Generally, such composite materials have a density of the order of 1.50 to 1.60 g/cm³. The characteristics indicated hereinabove are obtained after machining, which differentiates them from the materials of the prior art which lose a large part of their characteristics during machining of the rings obtained, even when they are constituted by a composite material formed by fibers embedded in a resin since a machining occurs and the nature of the material is not designed in an appropriate manner to present the necessary, correctly oriented anisotropy.

In order that the technical characteristics and advantages of the present invention may be more readily understood, an embodiment will be described by way of non-limiting example, with reference to the accompanying drawings, in which.

Figure 1:
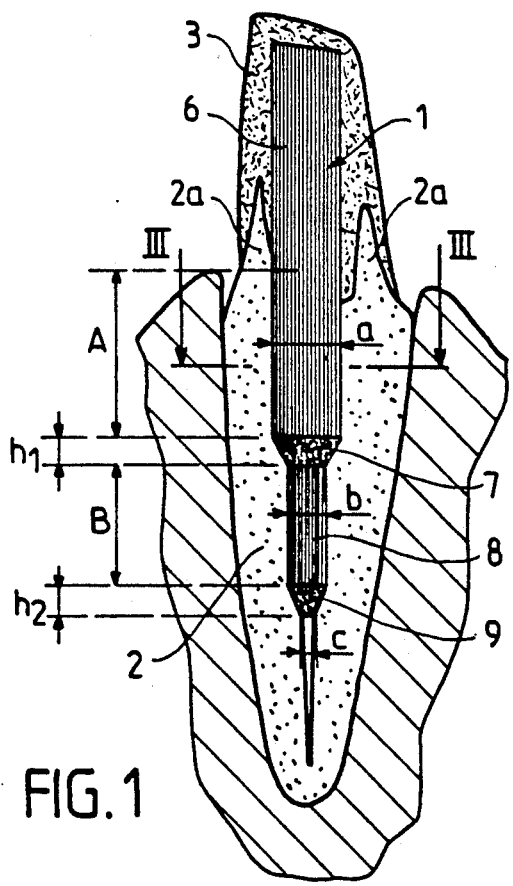
FIG. 1 is a view in vertical, longitudinal section of a crown-root reconstituting system according to the invention.

FIG. 1 shows a crown-root reconstituting system according to the invention, which is constituted by a physiological securing peg 1, made of a composite material, engaged and immobilized in a housing bored in the canal aperture of the root of a tooth 2, and by a block of crown reconstituting material 3 formed on the upper part of the peg 1, which projects above the root 2.

In order to obtain the securing peg 1, a ring of composite material is firstly made by pultrusion (or any other equivalent process), i.e. by extrusion of an epoxy resin 4 around a wick of continuous fibers 5 of high performance carbon, 8 micrometres in diameter, these fibers 5 representing from 40 to 80% and preferably 60% of the total volume on leaving the extruder, i.e. of the volume comprising the fibers and the resin after its solidification. The fibers 5 are equally tensioned and with unidirectional longitudinal arrangement in the axis of the peg 1, they are neither looped nor covered and, in addition, they are lightly prestressed in traction.

In a particularly advantageous embodiment of the invention, the equally tensioned fibers occupy 64% of the total volume or the total weight as the density of these fibers is substantially equal to that of the epoxy resin 4. This very high rate of fibers gives the peg 1 exceptionally high values in shear (shear strength: 170 MPa) which avoid any fracture of the peg, under normal physiological conditions. Its compressive strength, which is 440 MPa, locates it slightly above the associated dental structures. Furthermore, the anisotropy of mechanical behaviour of the material of the peg 1 has made it possible to reproduce with much similitude the decrement of the modulus of elasticity of the crown dentine to the root dentine, viz. 80 GPa to 18 GPa, during occlusal interferences. Due to the anisotropy of the material constituting the peg, the modulus of elasticity in traction-compression is variable depending on the angle of application of the effort with respect to the axis of the fibers 5. This property is fundamental as it is this which modulates the effects of the stresses and makes it possible to increase without danger the surface of the peg/dentine interface. If the stress is perpendicular to the fibers, the modulus of elasticity is 8 GPa. If the stress makes an angle of 20° with respect to the transverse plane, the modulus of elasticity is 34 GPa. This is the most frequent case during the high stresses of chewing, those which provoke cracks and fractures at the instant when one grinds the food before the return into centred position. At that moment, the modulus of elasticity has an average value of 21 GPa which is very close to the modulus of elasticity of the root dentine (18 GPa).

The continuous ring of composite material such as defined above, which has a diameter equal to or greater than the largest diameter of the pegs which are to be obtained, is then machined, for example mechanically by slicing, in order to obtain a peg 1 having the shape shown in FIG. 1. This securing peg is constituted by a piece of revolution formed by two coaxial cylindro-conical parts in line with one another, namely an upper cylindro-conical part of large diameter and a lower cylindro-conical part of smaller diameter. The upper cylindro-conical part comprises a cylindrical shank 6, of relatively large diameter a, extended, at its lower end, by a truncated part 7 converging downwardly, with a small base of diameter b. Following this small base is a cylindrical shank 8 of diameter b which terminates in a truncated part 9, converging downwardly and whose small base has a diameter c. The upper cylindrical shank 6, of large diameter a, ensures a cylindrical retention inside the root 2 over a distance A of the order of 3 mm. The securing peg according to the invention also ensures a second cylindrical retention over the length B corresponding to the length of the cylindrical shank 8 of small diameter b. The truncated parts 7 and 9 which have respective heights h1 and h2, constitute steps of stabilization of the peg 1 in the root of the tooth 2.

In the securing peg as has just been described, the equally tensioned fibers extend in the longitudinal direction and they are continuous from one frontal face of the peg to the other, apart, of course, from the fibers which are cut in the truncated zones 7 and 9.

The following table gives the values of the dimensions, in mm, of various pegs which have given entire satisfaction during the tests which were run.

| | | | |
|---|---|---|---|
| Diameter a: | 1.4 | 1.8 | 2.1 |
| Diameter b: | 1 | 1.2 | 1.4 |
| Diameter c: | 0.65 | 0.85 | 0.85 |
| Height h1 | 1 | 1 | 1 |
| Height h2 | 1 | 1 | 1 |
| Length B: | 2.5 | 3 | 3.5 |

Figure 2:
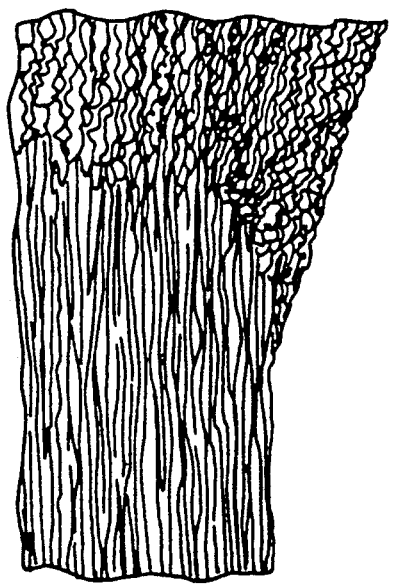
FIG. 2 is a schematic reproduction of a micrograph of part of the peg of the system according to the invention, obtained by means of an electronic scanning microscope with an enlargement of 500.
Figure 4:
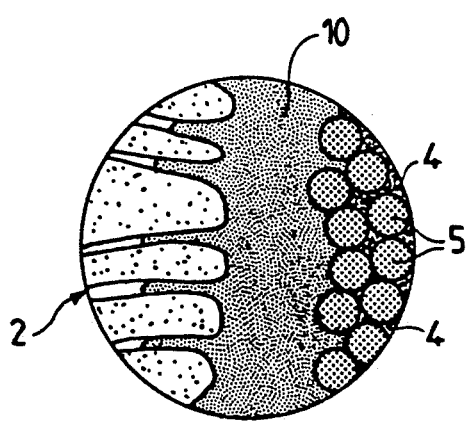
FIG. 4 is a view in transverse section, on a still larger scale, of part of the root of a tooth and of the securing peg.

As is more clearly apparent from FIGS. 2 and 4, the peg obtained after slicing presents an irregular surface on which are regularly distributed elements in relief which never exceed 10 to 20 micrometers but whose presence is constant. They are due, at the level of the truncated steps of stabilization 7, 9 of the plug, to the oblique section (30°) of the carbon fibers 5 further to the machining and, on the cylindrical parts, by grooves between the fibers 5 having remained very firmly fixed to the matrix of the epoxy resin 4, which thus creates anfractuosities which perfectly duplicate the prepared dentine surface.

Figure 3:
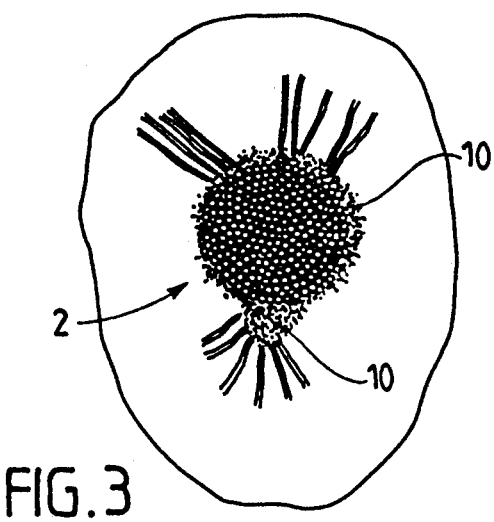
FIG. 3 is a partial view in horizontal, transverse section, on a larger scale, made along line III—III of FIG. 1.

The elements in relief on the surface of the peg 1 give the latter a superficial roughness improving the adherence of a glue 10 (FIGS. 3 and 4) with which the dentine surfaces and the peg are coated before said peg is placed in the housing previously opened in the canal aperture.

The crown-root reconstituting system also comprises, as shown in FIG. 1, a joining element 3 between the peg 1 and the remaining sound dentine walls 2a to terminate the reconstruction of the loss of substance and to match the individual morphology. The crown reconstituting material 3 used to that end is a self-polymerizing polyurethane-acrylic resin filled with short lubricated glass fibers (having undergone a specific surface treatment to bind them firmly to the polyurethane acrylic matrix), 200 micrometers in length and 9 micrometers in diameter (60% by weight and 70 to 80% by volume). These short fibers are disposed at random in the mass of the material 3. The mechanical properties of the reconstituting material 3 have been established to allow damping of the stresses and durable bonds between the peg 1 and the sound dentine walls 2a. Its very low modulus of elasticity (3.7±0.3 GPa) gives it properties of elasticity which make it a primary damper of stresses during the first dento-dental shocks. This property has been very clearly evidenced during mechanical tests in compression and bending where the test pieces were seen to exceed the breaking limit, without apparent modification of the outer volume, in 30% of the cases. Its compressive strength is close to that of the crown dentine (220±20 MPa).

Its water absorption coefficient is 0.3% and its setting time is between 3 and 4 minutes. This material is in addition chemically compatible with the carbon/epoxy composite material, which enables it to establish solid interfaces consolidated by the surface micro-roughness of the peg which adds the effects of a micro-keying to the chemical bond.

From the foregoing description, it is seen that the mechanical properties of the components of the crown-root reconstituting system according to the invention are the closest possible to one another, particularly concerning the transverse modulus of elasticity which is very close to that of the dentine. From this homogeneity of the behaviour there follows a good cohesion between the components as well as a lesser fatigue of the interfaces. The reconstitution material 3 performs the role of primary damper of the stresses and such damping is completed in the peg 1 by the fact that its modulus of elasticity, for the stresses exerted in the angular zone from 0° to 20° with respect to a transverse plane, has an average value substantially equal to that of the dentine.

We claim:

1. A crown-root reconstituting system for a tooth including a root having a root denture with a modulus of elasticity of 18 GPa, comprising:

a physiological dental securing peg (1) of a composite material, said peg (1) including an element of revolution formed from a wick of high strength fibers (5) embedded in a resin (4) forming an epoxy resin matrix, said fibers (5) being parallel to one another, elongated in the axial direction of said peg (1), continuous from one end of said peg to the other end thereof, in the central part of said peg;

a crown reconstituting material (3) adapted to be placed between peg (1) and said sound dentine walls (2a); and means for providing a transverse modulus of elasticity on the order of magnitude of the average of that of dentine in the amount of 18 GPa which is very close to the modulus of elasticity of the root denture and a longitudinal compression-tensile strength of 440 MPa and a shear strength of 170 MPa which is greater than corresponding average values for dentine wherein all of said fibers are equally tensioned and pre-stressed.

2. The crown-root reconstituting system according to claim 1, wherein said fibers (5) as a unit constitute from 40% to 80% of the total volume of the peg (1).

3. The crown-root reconstituting system according to claim 2, wherein said peg is formed by two coaxial, cylindro-conical parts of different diameters, each said cylindro-conical part including a cylinder (6, 8) followed by a frustrum of a cone (7, 9) converging towards the apex of said peg, and said peg (1) further comprising an irregular surface comprising relief elements having a depth in the range of 10 to 20 micrometers, said elements relief being formed by oblique sections of the fibers, and, said relief elements formed on the cylinders, by grooves between the fibers (5).

4. The crown-root reconstituting system according to claim 1, wherein said peg is formed by two coaxial, cylindro-conical parts of different diameters axially aligned with each other, each said cylindro-conical part including a cylinder (6, 8) followed by a frustrum of a cone (7, 9) converging towards the apex of said peg, and said peg (1) further comprising an irregular surface comprising relief elements having a debt in the range of 10 to 20 micrometers, said relief elements being formed by oblique sections of the fibers and, said relief elements formed on the cylinders, by grooves between the fibers (5).

5. The crown-root reconstituting system according to claim 4, wherein the fibers are pre-stressed in traction and the equally tensioned fibers occupy 64% of the total weight of the peg and the density of the fibers is substantially equal to the epoxy resin.

6. The crown-root reconstituting system according to claim 4, wherein the wick of fibers is 8 micrometers in diameter, and preferably comprises 60% of the total volume of the fibers and resin.

7. The crown-root reconstituting system according to claim 4, wherein one hundred percent of the fibers are continuous from one end of the peg to the other and are equally tensioned.

8. The crown-root reconstituting system according to claim 4, wherein said fibers are carbon fibers which have a transverse modulus of elasticity of 8.5 GPa for an angle of application of 0° of a traction effort with respect to the transverse direction, and a transverse modulus of elasticity of 34 GPa for an angle of application of 20° of a traction effort with respect to the transverse direction, thereby providing an average of 21 GPa in an angular range of 0° to 20° which corresponds to the average orientation of a stresses exerted on the tooth during chewing.

9. The crown-root reconstituting system according to claim 1, wherein said high strength fibers are carbon fibers embedded in said resin forming said epoxy resin matrix having a transverse modulus of elasticity of 8.5 GPa for an angle of application of 0° of a traction effort with respect to the transverse direction.

10. The crown-root reconstituting system according to claim 1, wherein said high strength fibers are carbon fibers embedded in said resin (4) forming said epoxy resin matrix having a transverse modulus of elasticity of 34 GPa for an angle of application of 20° of a traction effort with respect to the transverse direction.

11. The crown-root reconstituting system according to claim 1, wherein said fibers are carbon fibers embedded in said epoxy resin matrix and which have a transverse modulus of elasticity of 8.5 GPa for an angle of application of 0° of a traction effort with respect to the transverse direction, and a transverse modulus of elasticity of 34 GPa for an angle of application of 20° of the traction effort with respect to the transverse application of said means providing a modulus of elasticity, which provides an average of 21 GPa in an angular range of 0° to 20° which corresponds to an average orientation of the stresses exerted on a tooth during chewing.

12. The crown-root reconstituting system according to claim 1, wherein one hundred percent of the fibers are continuous from one end of the peg to the other and are equally tensioned.

13. The crown-root reconstituting system according to claim 1, wherein the fibers are pre-stressed in traction and the fibers and the epoxy resin are substantially equal to each other in density.

14. A process of manufacturing a physiological dental securing peg of a composite material, comprising extruding a resin (4) around a wick of continuous fibers (5) which are all equally tensioned and pre-stressed in traction;

allowing the resin to harden;

cutting a ring of composite material after the resin is hardened; and machining the peg by slicing so as to obtain two coaxial cylindro-conical parts of different diameters, in line with each other, each comprising a cylindrical shank (6, 8) followed by a respective truncated part of a frustrum of a cone (7, 9) converging towards the apex of the peg.

15. The method of claim 14, wherein the characteristics of the material are obtained after machining.

16. The crown-root reconstituting system according to claim 14, wherein the wick of fibers is 8 micrometers in diameter, and preferably comprises 60% of the total volume of the fibers and resin.

* * * * *